United States Patent [19]
Love et al.

[11] Patent Number: 5,609,600
[45] Date of Patent: Mar. 11, 1997

[54] TISSUE CUTTING DIE

[75] Inventors: Charles S. Love, Santa Barbara; Terrance J. Dahl, Solvang; Phillip J. Hudak, Goleta; Steven K. Lemp, Santa Barbara, all of Calif.

[73] Assignee: AUTOGENICS, Newbury Park, Calif.

[21] Appl. No.: 483,466

[22] Filed: Jun. 7, 1995

Related U.S. Application Data

[63] Continuation-in-part of Ser. No. 169,620, Dec. 17, 1993, Pat. No. 5,425,741.

[51] Int. Cl.$^6$ ............................................. A61B 17/32
[52] U.S. Cl. ............................................. 606/167
[58] Field of Search ............................. 606/1, 131, 132, 606/166, 167, 184; 128/750–758; 30/301, 316, 358; 83/531; 623/2

[56] References Cited

U.S. PATENT DOCUMENTS

| | | |
|---|---|---|
| 2,822,819 | 2/1958 | Geeraert . |
| 2,922,437 | 1/1960 | Rippingille . |
| 3,026,823 | 3/1962 | Wilcox . |
| 3,532,016 | 10/1970 | Lane . |
| 3,548,418 | 12/1970 | Angell et al. . |
| 3,570,014 | 3/1971 | Hancock . |
| 3,613,242 | 10/1971 | Hill et al. ................................ 606/132 |
| 3,714,671 | 2/1973 | Edwards et al. . |
| 3,755,823 | 9/1973 | Hancock . |
| 3,967,645 | 7/1976 | Gregory . |
| 3,983,581 | 10/1976 | Angell et al. . |
| 4,011,947 | 3/1977 | Sawyer . |
| 4,035,849 | 7/1977 | Angell et al. . |
| 4,065,816 | 1/1978 | Sawyer . |
| 4,084,268 | 4/1978 | Ionescu et al. . |
| 4,101,031 | 7/1978 | Cromie . |
| 4,172,295 | 10/1979 | Batten . |
| 4,182,446 | 1/1980 | Penny . |

(List continued on next page.)

FOREIGN PATENT DOCUMENTS

| | | |
|---|---|---|
| 5796865 | 10/1966 | Australia . |
| 1243453 | 10/1988 | Canada . |
| 0051451 | 5/1982 | European Pat. Off. . |
| 0116236 | 8/1984 | European Pat. Off. . |
| 0179562 | 4/1986 | European Pat. Off. . |
| 2391708 | 12/1978 | France . |
| 1952454 | 10/1969 | Germany . |
| 3612605 | 4/1986 | Germany . |
| 1189399 | 4/1970 | United Kingdom . |
| 1264472 | 2/1972 | United Kingdom . |
| 1598112 | 2/1978 | United Kingdom . |
| 2046165 | 11/1980 | United Kingdom . |
| 2169386 | 1/1986 | United Kingdom . |
| 9115167 PCT/ | 10/1991 | WIPO . |
| US9414699 | 12/1994 | WIPO . |

OTHER PUBLICATIONS

Barratt–Boyes, "A Method for Preparing and Inserting a Homograft Aortic Valve", Brt. J. Surc, Nov. 1965, vol. 52, No. II, pp. 847–856.

(List continued on next page.)

*Primary Examiner*—Guy V. Tucker
*Assistant Examiner*—William W. Lewis
*Attorney, Agent, or Firm*—Knobbe, Martens, Olson & Bear, LLP

[57] ABSTRACT

The present invention provides a novel tissue cutting device which accurately cuts the tissue to a predetermined configuration in a minimal amount of time, and where the tissue may then be used in an autologous heart valve. The disposable tissue cutting die of the present invention is comprised of a cutting die assembly and a cutting base assembly. The cutting die assembly retains a continuous blade with razor sharpened edges that enclose a desired spatial configuration. The cutting base assembly includes a rotatable cutting pad on which the tissue to be cut may be placed. The cutting die assembly and cutting base assembly are adpated to cooperate to cut the tissue when the cutting die assembly is inserted into the cutting base assembly and rotated approximately 180 degrees.

19 Claims, 12 Drawing Sheets

U.S. PATENT DOCUMENTS

| | | |
|---|---|---|
| 4,192,020 | 3/1980 | Davis et al. . |
| 4,211,241 | 7/1980 | Kaster et al. . |
| 4,247,292 | 1/1981 | Angell . |
| 4,297,749 | 11/1981 | Davis et al. . |
| 4,388,735 | 6/1983 | Ionescu et al. . |
| 4,470,157 | 9/1984 | Love . |
| 4,490,859 | 1/1985 | Black et al. . |
| 4,501,030 | 2/1985 | Lane . |
| 4,512,471 | 4/1985 | Kaster et al. . |
| 4,535,819 | 8/1985 | Atkinson et al. . |
| 4,597,767 | 7/1986 | Lenkei . |
| 4,605,407 | 8/1986 | Black et al. . |
| 4,643,732 | 2/1987 | Pietsch et al. . |
| 4,655,773 | 4/1987 | Grassi . |
| 4,679,556 | 7/1987 | Lubock et al. . |
| 4,687,483 | 8/1987 | Fisher et al. . |
| 4,692,164 | 9/1987 | Dzemeshkevich et al. . |
| 4,725,274 | 2/1988 | Lane et al. . |
| 4,801,015 | 1/1989 | Lubock et al. . |
| 4,838,288 | 6/1989 | Wright et al. . |
| 4,865,033 | 9/1989 | Krumeich et al. . |
| 4,881,562 | 11/1989 | Wright et al. . |
| 5,037,434 | 8/1991 | Lane . |
| 5,147,391 | 9/1992 | Lane . |
| 5,163,955 | 11/1992 | Love et al. . |
| 5,306,279 | 4/1994 | Atkinson .................................. 606/132 |
| 5,326,370 | 7/1994 | Love et al. . |
| 5,425,741 | 6/1995 | Lemp et al. ............................ 606/167 |

OTHER PUBLICATIONS

Reis, et al., "The flexible stant: A new concept in the fabrication of tissue heart valve prostheses"; The Journal of Thoracic and Cardiovascular Surgery, Nov. 1971, vol. 62, No. 5, pp. 683–689; 693–695.

Yates, "A fascial frustum valve for aortic valve–replacement", Thorax, 1971, vol. 25, pp. 184–189.

Brownlee, et al., "A fascia lata mitral valve based on the 'frustum' principle", Thorax, 1971, vol. 26, pp. 284–287.

Bartek, et al., "Frame–mounted tissue heart valves: technique of construction", Thoraz, 1974, vol. 29, pp. 51–55.

Ionescu, et al., "Replacement of heart valves with frame–mounted tissue grafts", Thorax, 1974, vol. 29, pp. 56–57.

Black, et al., "A construction technique for minimizing valve leaflet fatique failure in pericardial valves", Life Support Systems, Proceedings XI Annual Meeting ESAO, Alpbach–Innsbruck, Austria, Sep. 1984, vol. 2, Supp. 1.

Love, et al., "Degenerative calcification in tissue valves a metabolic/hemodynamic or immunologic problem?", Abstract published for the International Associate for Cardiac Biological Implants, Chicago, Apr. 5, 1987, p. 1.

Love, et al., "Experimental Evaluation of an Autogenous Tissue Heart Valve", Poster Presentation at the IV International Symposium Cardiac Bioprostheses, San Diego, Apr. 15, 1988.

Reul, et al., "In Vitro Testing of Bioprostheses", Trans. Am. Soc. Artif. Intern. Organs, 1988, vol. XXXIV, pp. 1033–1039.

Love, et al., "The Autogenous Tissue Heart Valve: Experience with Pericardium", Pericardial Tissue as a Cardiac Valve Substitute, Proceedings of a Symposium, Thumberbach, Austria, Sep. 1988, pp. 31–40.

Khan, et al., "Doppler and Hemodynamic Characteristics of the Autogogenics Bioprosthetic Valve", p. 1.

Love, et al., "Rapid Intraoperative Fabrication of an Autogenous Tissue Heart Valve: A New Technique", Proceedings of the Third International Symposium of Cardiac Bioprosthesis, Yorke Medical Books, New York, N.Y., 1986, pp. 691–698.

Love, "An Alternate Method for Applying a DACRON Cover to a Delrin Bioprosthetic Heart Valve Stent", Proceedings of the Third Southern Biomedical Engineering Conference, Pergamon Press, 1984, pp. 30–37.

Matsuda, et al., "A Hand–Made Valved Conduit with High–Porosity Knitted Graft and Glutaraldehyde–Treated Autologous Pericardial Trileaflet Valve", Abstracts of the VII World Congress Artificial Organs, 1989, vol. 13, No. 4.

TISSUE CUTTING DIE

CROSS-REFERENCE TO RELATED APPLICATION

This application is a continuation-in-part of our commonly assigned application, Ser. No. 08/169,620, filed on Dec. 17, 1993, now issued as U.S. Pat. No. 5,425,741, the entire disclosure of which is incorporated herein by reference.

FIELD OF THE INVENTION

This invention relates to cutting devices and is particularly directed to tissue cutting dies used to precisely and accurately cut various tissues to a particular predetermined configuration, particularly in the fashioning of an autologous tissue heart valve.

BACKGROUND OF THE INVENTION

Heart valves are typically replaced due to birth defects, stenosis (narrowing) of the valve (in which case the heart must exert a great deal of force to pump the blood through the valve) or insufficiency or incompetence of the valve, whereby the heart is unable to prevent backflow of the blood. The diseased or damaged heart valve is removed from the patient and replaced with some type of artificial or prosthetic valve.

The three main types of prosthetic heart valves are mechanical, biological and homograft. A detailed description and background of these three types of prosthetic heart valves may be found in U.S. Pat. No. 5,163,955, assigned to Autogenics, assignee of the present application and incorporated herein by reference. These valves, however, have proven to be costly and present an increased risk to the patient with respect to durability and acceptability.

Most recently, autologous tissue valves, i.e. valves constructed with the patient's own tissue, have been investigated. However, since this type of valve utilizes the patient's own tissue, the valve must usually be assembled during the same surgical procedure in which the patient's diseased or damaged valve is removed. Therefore, valve assembly must be completed in a rapid and efficient manner to avoid further risk to the patient.

To construct an autologous heart valve, one typically fits or mounts the patient's tissue onto a stent or some other type of valve frame. This can be accomplished by several methods. In one conventional method, the individual valve leaflets are cut from a roughly sized piece of tissue and individually sewn or attached onto the frame. In another method, a single piece of roughly sized tissue is attached to the valve frame and the excess tissue is trimmed away. Both of these methods, however, have proven to be time-consuming and unreliable.

The above referenced '955 patent discloses a novel and substantially improved cutting die for quickly and precisely cutting autologous tissue into the desired configuration. This die, however, does not provide the major improvements and advantages which have been incorporated into the cutting die of the present invention. These advantages will become apparent from the Detailed Description of the Invention, considered together with the drawings and claims.

SUMMARY OF THE INVENTION

The present invention provides a new tissue cutting device for autologous tissue heart valves which is a modification of the die disclosed in the '955 patent.

In one preferred embodiment, the tissue cutting die of the present invention comprises a cutting die assembly and a cutting base assembly. The cutting die assembly includes a handle with a plurality of attachment points, a first blade retainer, and a second blade retainer, which are secured to the handle at the attachment points. Screws or other types of attachments are provided to secure the handle to the blade retainers.

An insert is positioned within the blade retainers so that a narrow gap exists between the insert and the blade retainers. Preferably, the insert has a shape corresponding to the spatial configuration into which the tissue will be cut.

A blade with a razor sharpened edge is retained within the gap between the insert and the blade retainers, with the blade edge extending above the surface created by the insert and the blade retainers.

The cutting base assembly is adapted to receive the cutting die assembly. The cutting base assembly includes a cutting base having a substantially circular upper surface and a molded lower surface. The upper surface has a raised portion which forms a cutting bump. A circular cutting pad with an upper face and a lower face is positioned on the upper surface of the cutting base and is rotatable thereon. An annular cutting die guide is fixedly secured to the upper surface of the cutting base, so that the cutting pad is rotatably retained between the cutting base and the cutting die guide.

When the cutting die assembly is inserted into the cutting base assembly, the blade edges contact the tissue on the cutting pad. As the cutting die assembly and pad are rotated with respect to the cutting base, the cutting bump forces the cutting pad into the blade edges, so that the tissue is cut to the predetermined configuration.

A significant feature of the present invention is that a consistent cutting force is applied between the tissue to be cut and the cutting blade. Importantly, this cutting force is substantially independent of the force applied by the operator. Thus, different operators will achieve the same consistent cutting results using the present invention.

Another important feature of the invention is that the tissue is not only cut extremely accurately, but also very quickly. This is an especially important advantage when the tissue being cut is to be used to construct a heart valve during the open heart surgery procedure.

BRIEF DESCRIPTION OF THE DRAWINGS

FIG. 1a is an enlarged partial view of the tissue cutting die illustrated in FIG. 1 at a—a.

DETAILED DESCRIPTION OF THE INVENTION

Figure 1:
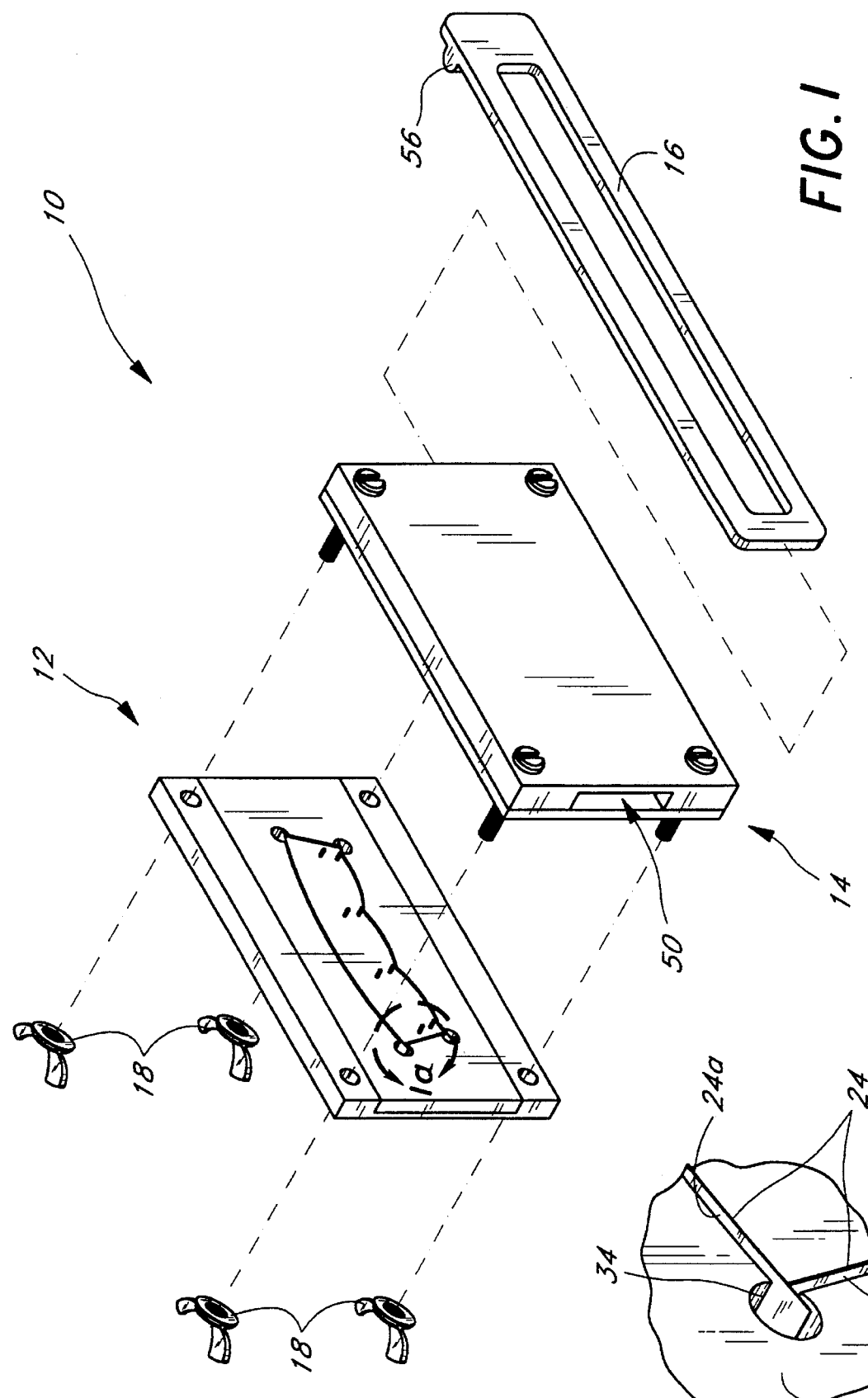
FIG. 1 is an exploded perspective view of the tissue cutting die of the present invention.

FIG. 1 illustrates an exploded view of the disposable tissue cutting die 10 of the present invention for precisely and accurately cutting tissue to a predetermined configuration for use in a medical prosthetic device such as an autologous heart valve. As discussed in detail below, the tissue to be precisely cut is placed onto the base member 14 and contacts the cutting blade 24 supported by the cover 12 when the tissue is locked between the cover 12 and the base member 14. The slide 16 is then translated through a tunnel 50 of the base member 14 to force the tissue between ridge 56 of slide 16 and the cutting blade 24 so as to precisely cut the tissue to conform to the space defined by the cutting blade 24.

Figure 2:
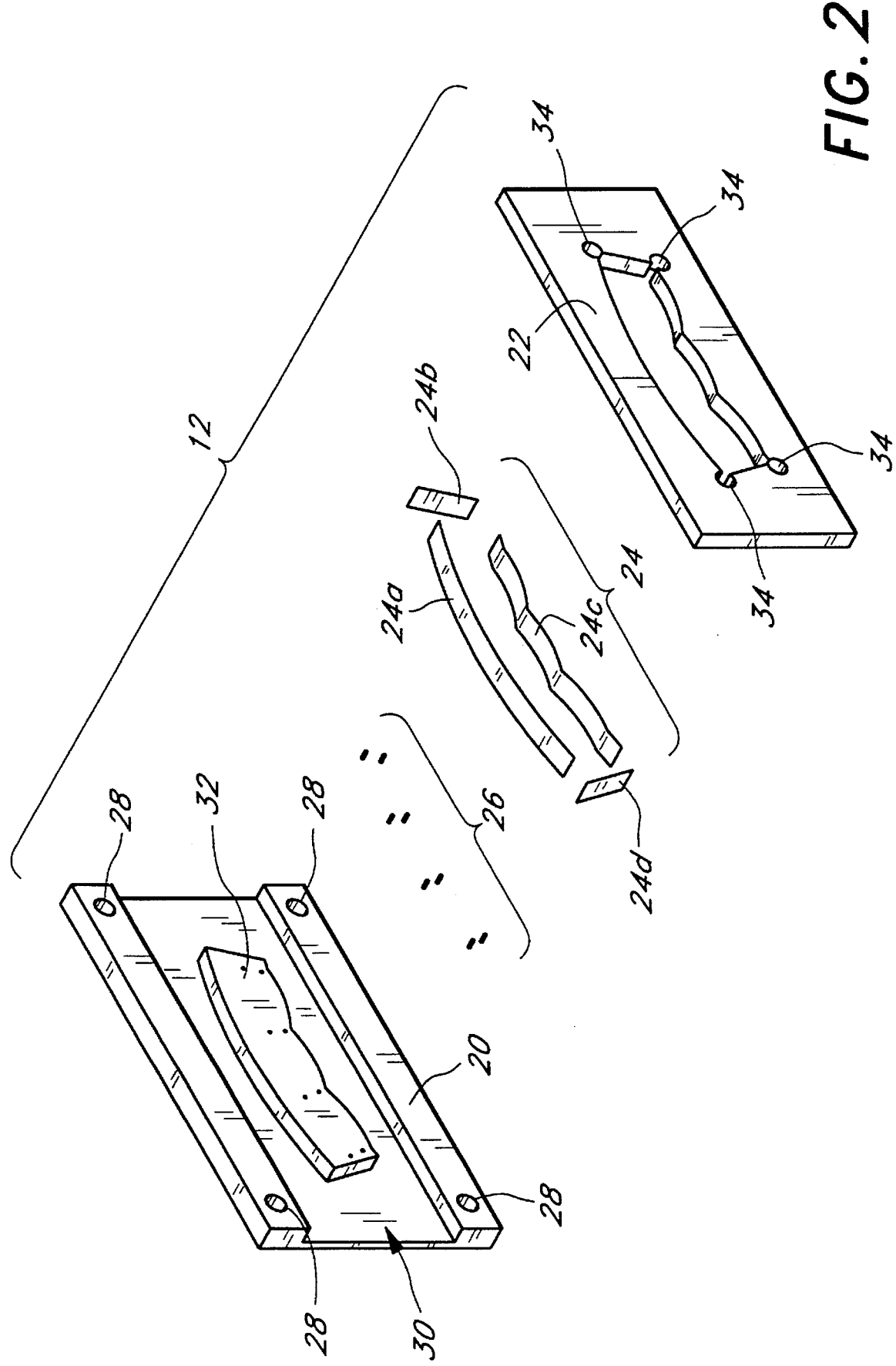
FIG. 2 is an exploded perspective view of the cover of the tissue cutting die of FIG. 1.

Referring to FIG. 2, the cover 12 includes top member 20, insert 22, cutting blade 24 and four pairs of ferrules 26. In the preferred embodiment, the top member 20 is made of a translucent polycarbonate material, preferably of biomedical grade. This top member 20 is generally rectangular in shape and has four through holes 28 located at the four corners of the top member 20. The holes are used to align and attach the cover 12 to the base member 14.

A channel 30 runs the length of top member 20 and projects into the channel 30 to form an island 32 in the middle of the top member 20. The outer periphery this island 32 is an outline of the desired cut tissue piece.

The preferred embodiment of the heart valve disclosed and claimed in the '955 patent provides an inner stent having tissue alignment members. Accordingly, the preferred embodiment of this invention includes four pairs of ferrules 26 embedded within the polycarbonate material of the island 32, the location of these ferrules 26 corresponding to the location of the tissue alignment members of the heart valve inner stent. Ferrules 26 typically extend approximately 35 mils above the top surface of the island 32. In addition, the diameter of the ferrules 26 corresponds to the diameter of the tissue alignment members.

Cover 12 further includes an insert 22, made of semi-translucent polycarbonate material, constructed so as to fit within the channel 30 and completely surround the island 32 of the top member 20. The gap between the edges of the island 32 and the insert 22 is large enough so as to accommodate and retain the cutting blade 24. In one embodiment, the insert 22 is precisely configured so that a gap of 0.002 inch or less exists between the edges of the insert 22 and the top member 20. In addition, the insert 22 has four through holes 34 located at the corresponding locations of the four corners of the island 32.

Cutting blade 24 is fixedly retained within the narrow gap between the island 32 and the insert 22. Cutting blade 24 is advantageously formed from four discrete blades 24a, 24b, 24c, 24d. These blades are advantageously formed from thin case hardened corrosion resistant steel having sufficient flexibility to conform to the shape of the gap located between the island 32 and the insert 22. The blade thickness should, however, be sufficient to prevent deflection of the blade and, consequently, an inadequately cut piece of tissue. In the preferred embodiment, the blades 24a–24d were made from a strip of 0.006 inch thick stainless steel, supplied by American Safety Razor of West Virginia, having a razor-sharpened edge. That razor-sharpened edge extends 35 mils above the top surfaces of the island 32 and the insert 22.

A significant feature of the invention is that the four corners of the space defined by the island 32 and the cutout portion of insert 22 are relieved by four through holes 34 in the insert 22. As shown in FIGS. 1 and 1a, the end of the blade 24a extends into a through hole 34 with the adjoining blade 24d abutted up against. Without this relief of this cutout portion, the precise juncture of the two blades 24a, 24d would involve such tight tolerances that manufacturing practices typically dictate a slight gap between the blades. Dies constructed with gaps between adjoining blades leave a small segment of uncut tissue at the corners of the opening, requiring a manual cut after opening of the die to separate the two pieces of tissue. In contrast, the present invention merely involves making each blade 24a–24d slightly longer than the actual perimeter of the island 32, with the excess blade 24a extending into one of the holes 34.

Figure 3:
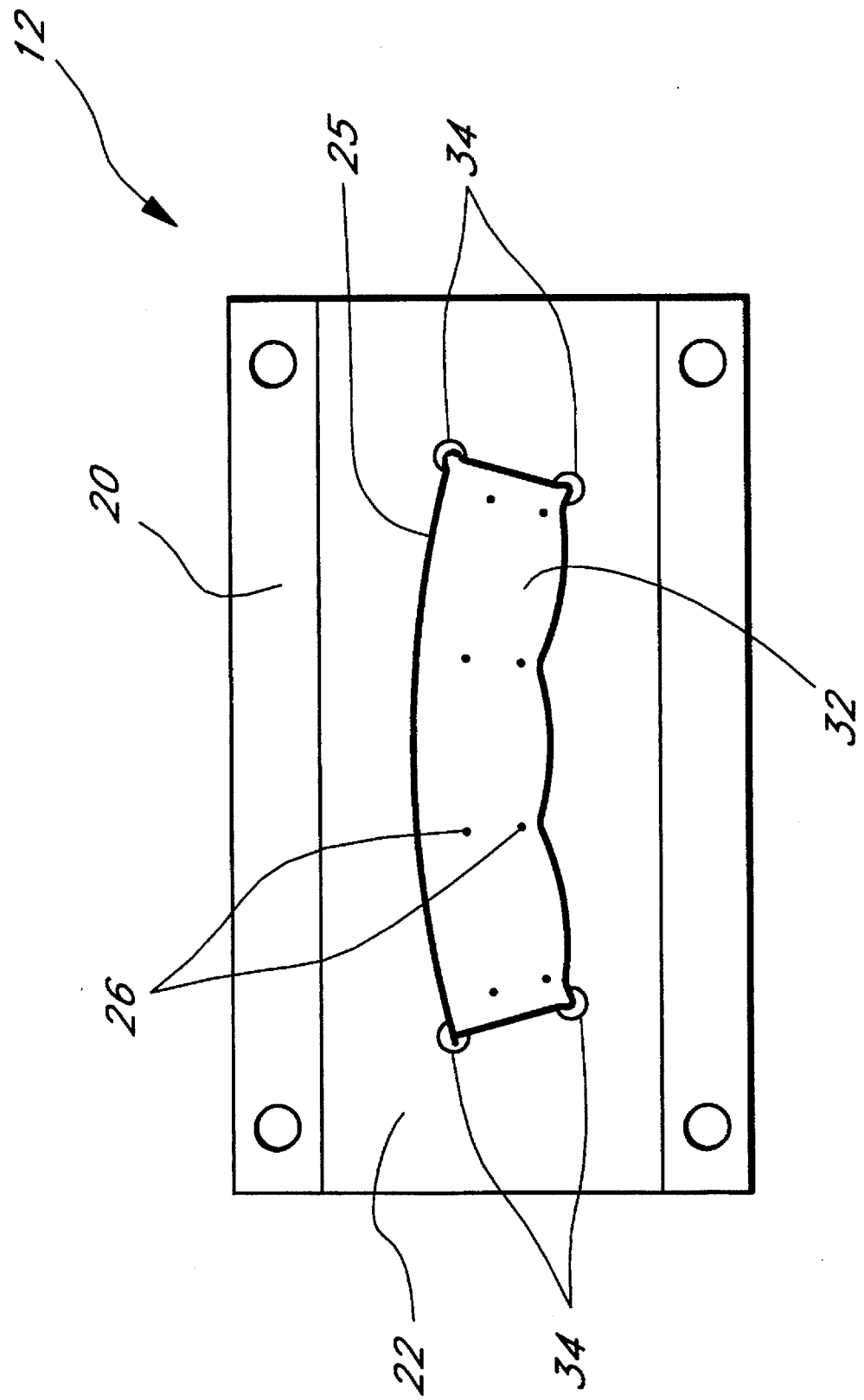
FIG. 3 is a front view of an alternate embodiment of the cover of the tissue cutting die with a one piece blade.

Alternately, a flexible, one piece blade 25 is used to precisely cut the piece of tissue. As shown in FIG. 3, the four through holes 34 in the insert 22 provide an additional advantage in that they allow the cover 12 to accommodate a flexible one piece blade 25. Thus, the relief provided by the radius of the through holes 34 allows a single continuous blade 25 to bend around each of the four corners of the island 32. Without the relief provided by these through holes 34, the otherwise close tolerances at the corners of the island 32 would make it difficult to accommodate a one piece blade 25. Thus, with the relief, a one piece blade 25 would have to be precisely bent to the angle formed at each of the four corners of the island 32 and still fit within the narrow gap between the island 32 and the insert 22. Therefore, the through holes 34 provide substantial additional space to allow the one piece blade 25 to bend around each of the four corners of the island 32.

Figure 4:
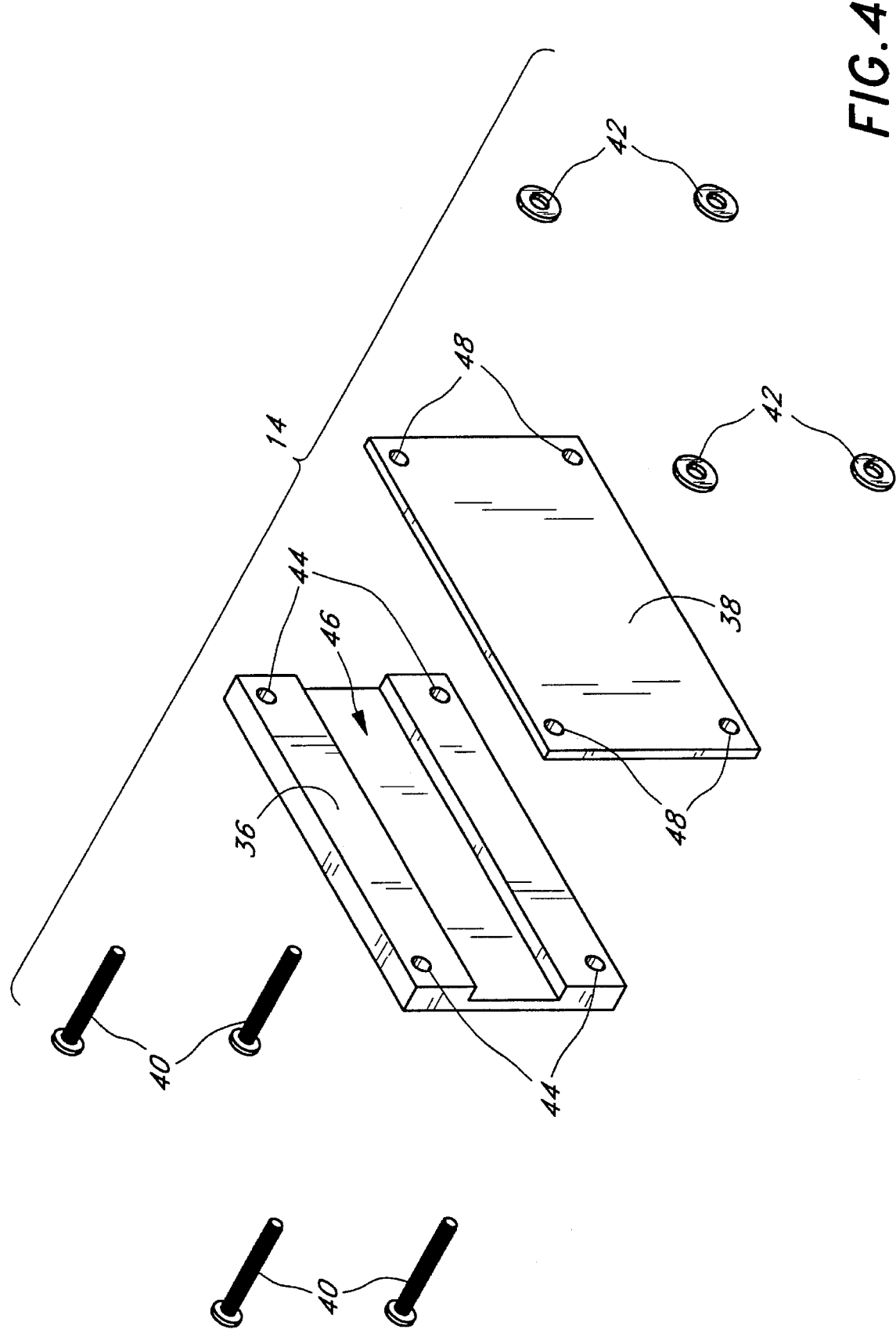
FIG. 4 is an exploded perspective view of the base member of the tissue cutting die of FIG. 1.

FIG. 4 shows an exploded perspective view of the base member 14 of the tissue cutting die 10 of the present invention, including a base piece 36, a thin flexible sheet 38, four threaded screws 40 and four washers 42. The base piece 36 of the base member 14 is advantageously made of a translucent polycarbonate material, preferably biomedical grade. The base piece 36 is generally rectangular in shape and has four threaded through holes 44 located at the four corners of the base piece 36.

A channel 46 is provided along the center length of the base piece 36 of the base member 14. The width of the channel 46 in the base piece 36 of the base member 14 accommodate the width of the island 32 and, therefore, is slightly wider than the width of the island 32.

The thin flexible sheet 38 of the base member 14 provides the cutting pad of the tissue cutting die 10. This thin flexible sheet 38 is generally 0.032 inch thick or less. TEFLON is the preferred material for sheet 38 due to its smooth surface characteristic which provides the correct amount of adhesion for the tissue. The thin flexible sheet 38 is generally rectangular in shape and is similar in size (i.e. length and width) to the top member 20 of the cover 12 and the base piece 36 of the base member 14. Located at the four corners of the thin flexible sheet 38 are four through holes 48. The location of the through holes 48 in the thin flexible sheet 38 corresponds to the location of the through holes 44 in the base piece 36 of the base member 14.

Four threaded screws 40, as shown in FIG. 4, are used to attach the thin flexible sheet 38 to the surface of the base piece 36 of the base member 14. Each screw 40 enters through the bottom surface of the base piece 36 of the base member 14 and extends through the top surface of the thin flexible sheet 38. Due to the channel 46 provided along the center length of the base piece 36 of the base member 14, the thin flexible sheet 38 creates a tunnel 50 in the base member 14, as shown in FIG. 1.

A washer 42 is positioned onto each of the screws 40 and rests on the surface of the thin flexible sheet 38. The thickness of the washers 42 is determined by the height by which the blades 24a–24d extend above the surfaces of the island 32 and the insert 22. Thus, by way of specific example, if the blades 24a–24d extend 35 mils above the surfaces of the island 32 and the insert 22, then the washers 42 must be at least 35 mils in thickness. This is to ensure that the blades 24a–24d are not damaged by the thin flexible sheet 38 during shipment of the assembled tissue cutting die 10. In addition, the washers enable the blades 24a–24d to securely hold the piece of tissue between the cover 12 and the base member 14, without actually cutting the tissue. In this specific example, the maximum thickness of the washers 42 is calculated by adding the blade height (35 mils) and half of the nominal average tissue thickness (15–20 mils).

Figure 5:
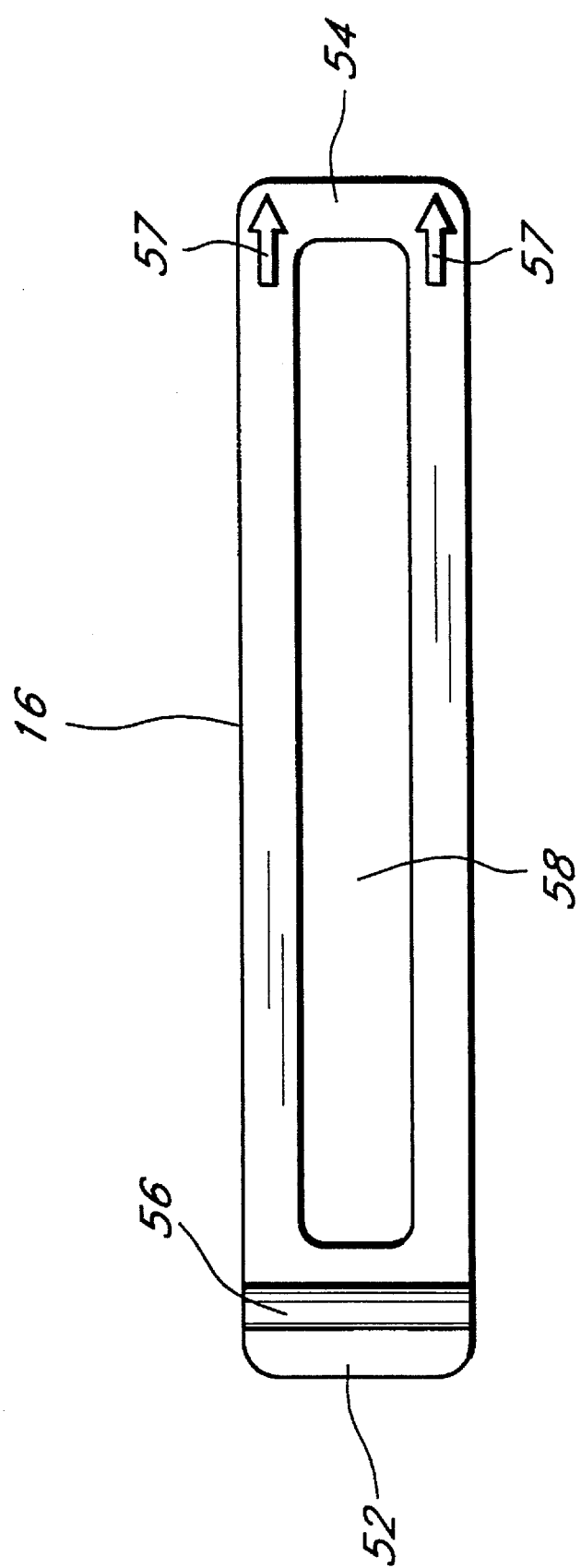
FIG. 5 is a top view of the slide of the tissue cutting die of FIG. 1.

FIG. 5 shows one embodiment of the slide 16 of the tissue cutting die 10 of the present invention. The slide 16 is longer in length but slightly narrower in width than the channel 46 in the base piece 36 of the base member 14. The slide 16 is advantageously made of thermoplastic and is similar in thickness to that of the thin flexible sheet 38. A "bump" 56 or raised portion is located on the top surface of the slide 16 near the end 52. The height of the bump 56 is equal to or slightly greater than the height of the tunnel 50 in the base member 14. The opposite end 54 of the slide 16 is generally flat. In the embodiment shown, slightly raised "arrow" symbols 57 are located on the top surface of the slide 16 near its end 54. The middle or cut-out portion 58 of the slide 16 is cut out, in the embodiment shown, so that the user's finger can be inserted within the cutout portion proximate to arrows 57 to obtain a firmer grasp of the slide 16, and thereby facilitate the pulling of the slide 16. The use of the slide 16 will be described in detail below.

Figure 6:
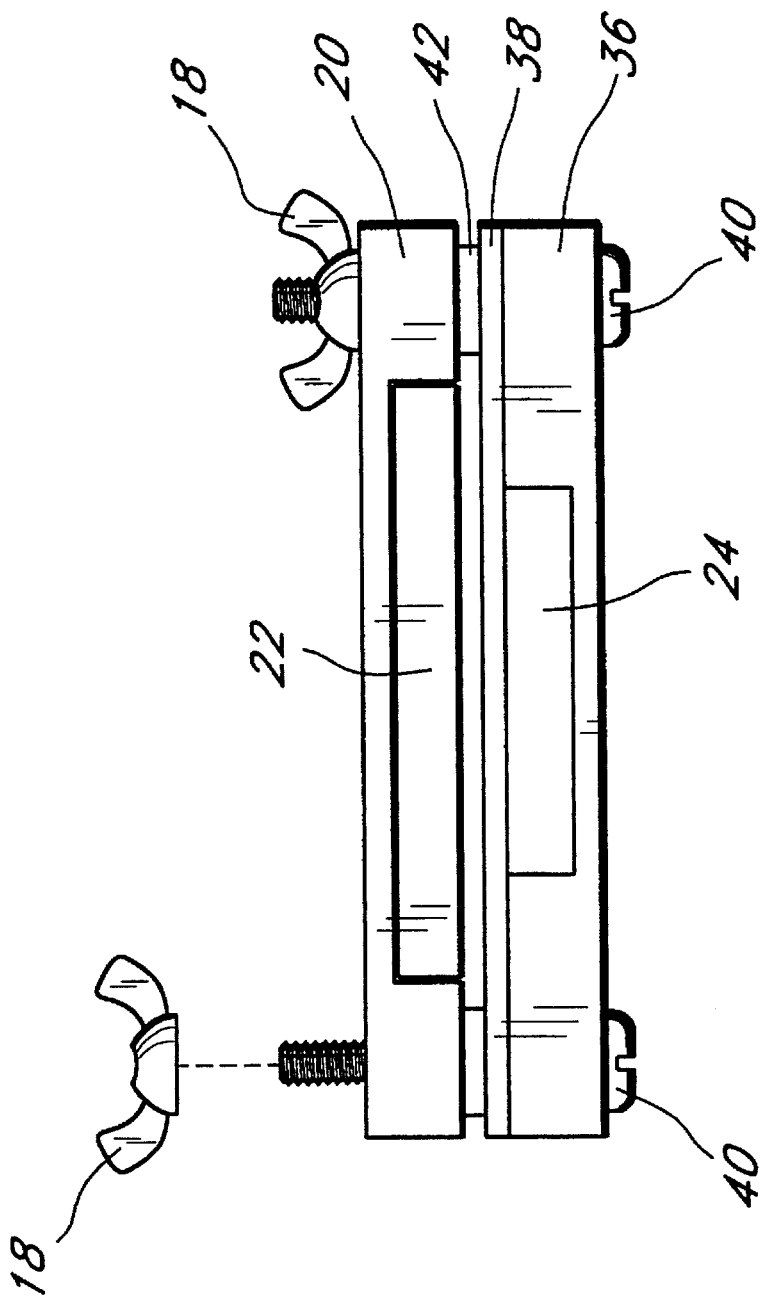
FIG. 6 is a side view of the partially assembled tissue cutting die of FIG. 1, with one wing nut screwed onto a threaded screw.

FIG. 6 illustrates a side view of the partially assembled tissue cutting die 10 of the present invention, with one of the four wing nuts 18 screwed onto one of the threaded screws 40. The wing nuts 18 are advantageously made of thermoplastic material and have a preformed internal thread. The wing nuts 18 are primarily used as a clamping means and, therefore, are of adequate size to allow one to easily and smoothly secure the wing nuts 18 onto the screws 40.

The tissue cutting die 10 illustrated in FIGS. 1–6 is used in the following manner. First, a roughly sized piece of tissue is laid flat across the top surface of the thin flexible sheet 38 of the base member 14. Due to the slipperiness of the patient's tissue and the adhesion characteristics of a material such as TEFLON, the tissue can be easily smoothed to lie flat across the thin flexible sheet 38. Next, the cover 12 is assembled onto the base member 14 so that the blades 24a–24d can contact the thin flexible sheet 38. This is accomplished by aligning the holes 28 located in the four corners of the cover 12 with the threaded ends of the screws 40 protruding out the top surface of the base member 14. In addition, the cover 12 and tissue are aligned so that the blades 24a–24d will cut the desired portion of the tissue.

Once the cover 12 is assembled onto the base member 14, the tissue is clamped between the two assemblies 12, 14 with the wing nuts 18. During this step, the blades 24a–24d may become slightly embedded into the tissue. However, due to the strength or toughness of the tissue, the blades 24a–24d normally do not completely penetrate the tissue.

The actual cutting of the tissue is accomplished by pulling the slide 16 through the entire length of the tunnel 50 of the base member 14. The second end 54 of the slide is pushed through one end of the tunnel 50 until it emerges out the opposite end of the tunnel 50. Due to the symmetry of the cover 12 and base member 14, the slide 16 may be pulled through either end of the tunnel 50, in the direction indicated by the "arrow" symbols 57 located on the second end 54 of the slide 16. The user of the tissue cutting die 10 pulls the second end 54 of the slide 16 until the first end 52 of the slide 16 is pulled along the entire length of the tunnel 50 and emerges out the other end of the tunnel 50. During this procedure, the bump 56, located on the first end 52 of the slide 16, pushes against the bottom surface of the thin flexible sheet 38. This, in turn, forces the tissue to be pushed against the blades 24a–24d and the ferrules 26 of the cover 12.

The bump 56 located on the first end 52 of the slide 16 produces a "wave" in the tissue and the thin flexible sheet 38. This "wave" allows one to sequentially push portions of the tissue into the blades 24a–24d, thereby enabling the blades 24a–24d to work in shear. Due to the angle between the four blades 24a–24d and the bump 56, all the blades 24a–24d are able to cut the tissue in shear.

After the tissue is cut, the wing nuts 18 are unscrewed from the threaded screws 40 so that the cover 12 may be carefully removed from the base member 14. The resultant, pre-configured cut piece of tissue is removed from the base member 14 and mounted onto the valve stent. The remaining excess tissue may be discarded.

Figure 7:
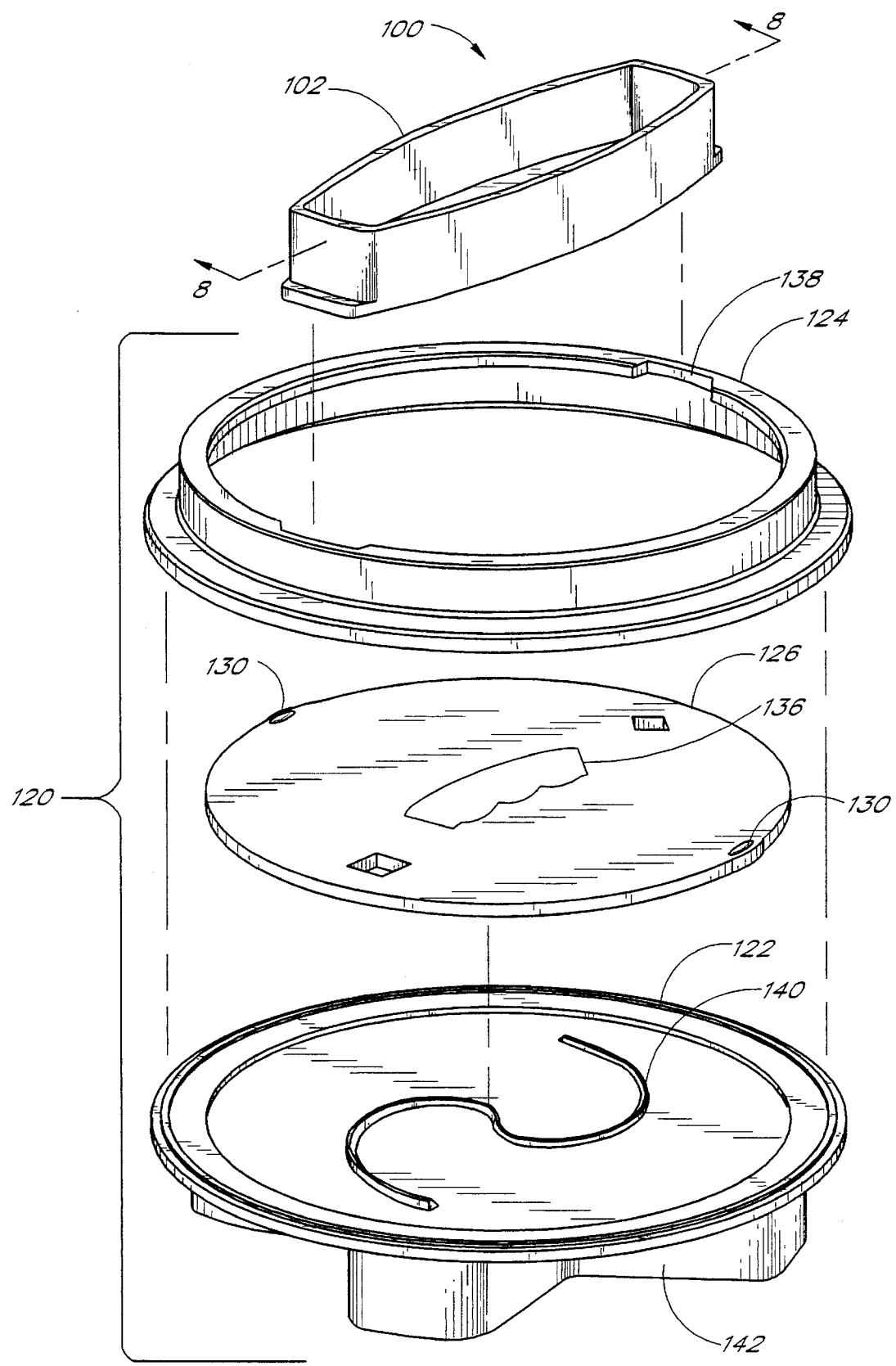
FIG. 7 is a partially exploded perspective view of the rotary tissue cutting die embodiment of the present invention.
Figure 8:
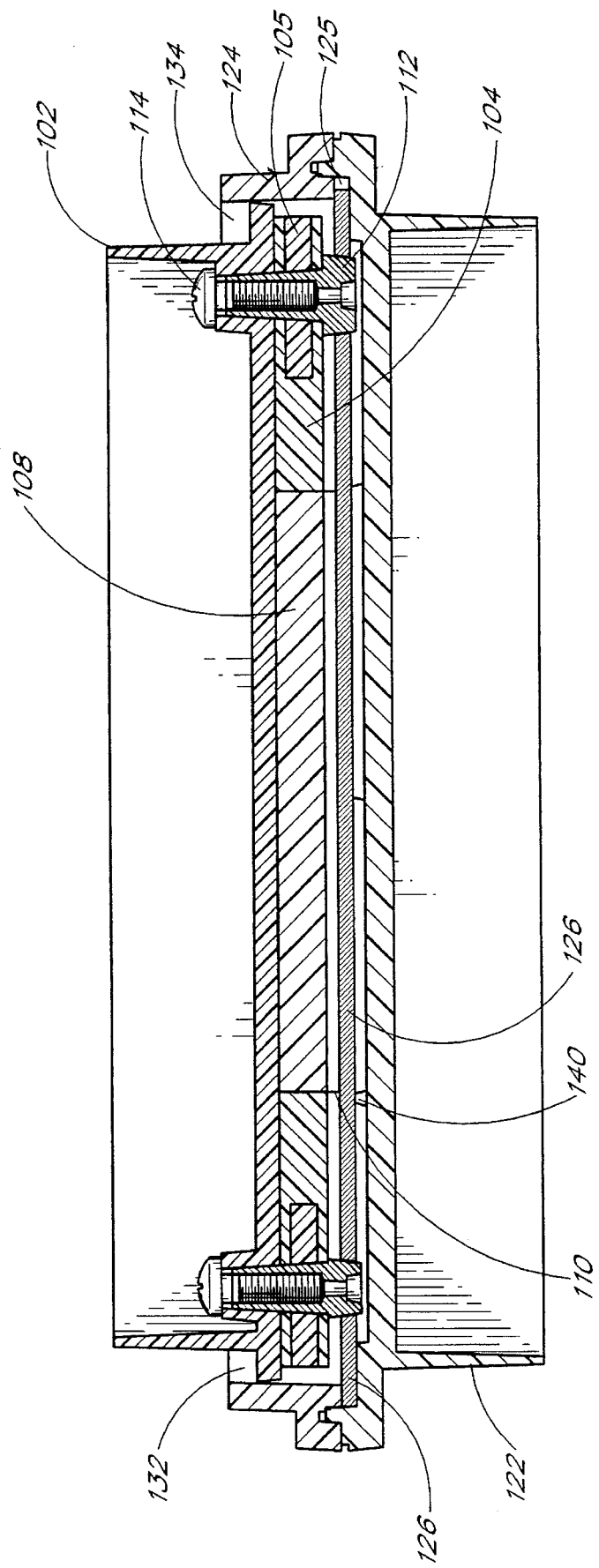
FIG. 8 is a cross-sectional view of FIG. 7 showing the cutting die assembly inserted into the cutting base assembly.

FIGS. 7 and 8 illustrate an alternative preferred embodiment of the disposable tissue cutting die of the present invention, which utilizes a rotary motion to initiate the cutting of the tissue to a predetermined configuration. As explained more fully below, the tissue to be cut is placed on the cutting base assembly 120 over the tissue alignment markings 136 on the rotatable cutting pad 126. The cutting die assembly 100 is then inserted into the cutting base assembly 120 through notches 138, and razor sharpened blades 110 extending downwardly from the cutting die assembly 100 contact the tissue to be cut. After insertion into the cutting base assembly 120, the cutting die assembly 100 and the cutting pad 126 are then rotated approximately 180 degrees. As the cutting die assembly 100, the cutting pad 126, and the tissue are rotated relative to the cutting base 122, a cutting bump 140 formed on base 122 sweeps the blade profile so that a force is directed against the bottom face of the the cutting pad 126 (i.e., the face shown in FIG. 8 juxtaposed next to cutting bump 140), progressively forcing the tissue to be cut into the entire peripheral configuration of blade 110, resulting in precision cutting of the tissue to the predetermined configuration.

Referring to FIGS. 9–12, there is depicted the preferred embodiment cutting die assembly 100 of the present invention. The cutting die assembly 100 includes a handle 102, a left-hand blade retainer 104, a right-hand blade retainer 106, an insert 108, cutting blades 110a–d, and four pairs of cutting ferrules 116. Handle 102, insert 108, and blade retainers 104 and 106 are preferably formed from a clear rigid biocompatible material such as translucent medical-grade polycarbonate. Advantageously, use of a clear material permits the clinician to see the tissue as the cutting operation is performed.

Figure 9:
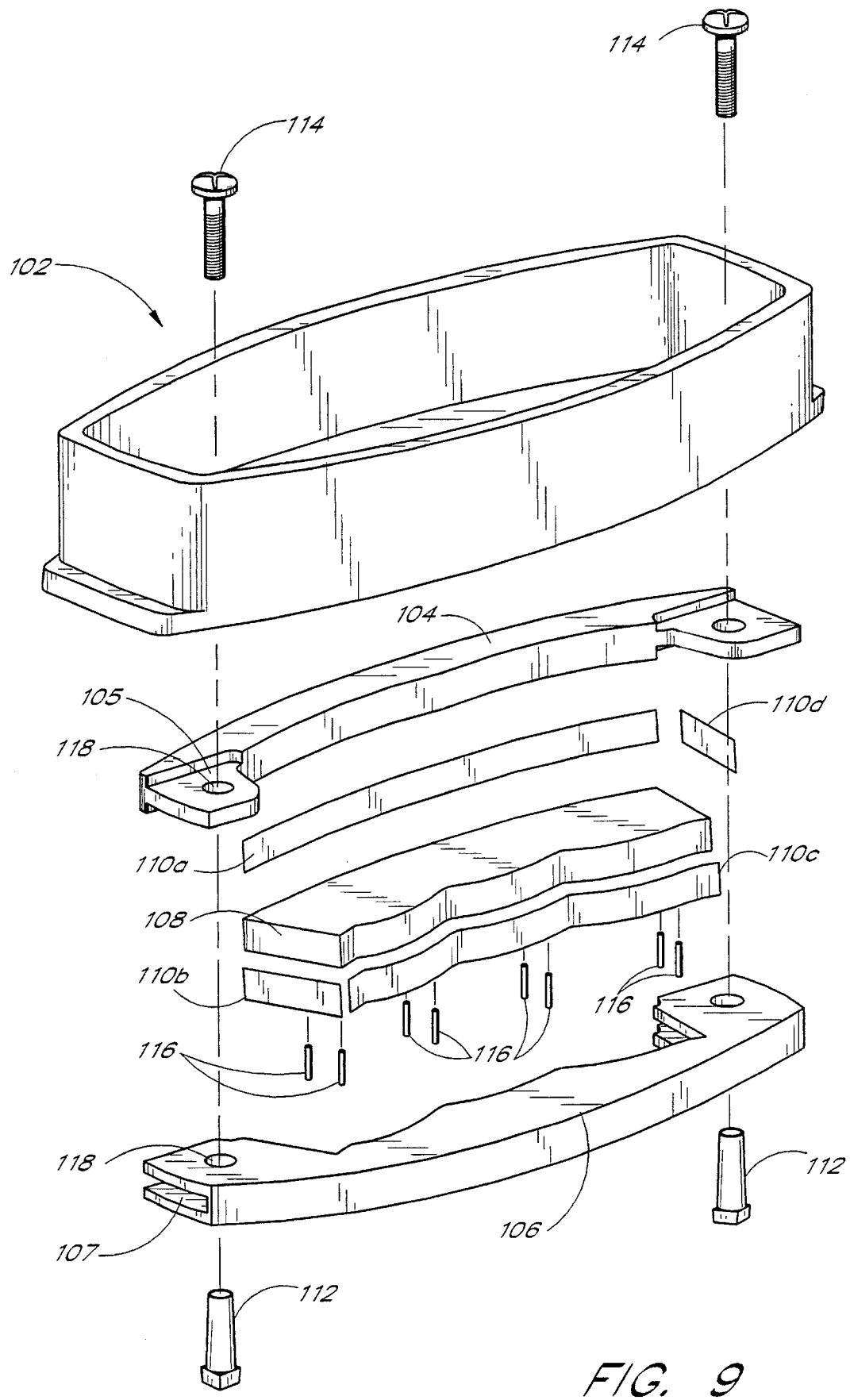
FIG. 9 is an exploded perspective view of the cutting die assembly of FIG. 7.
Figure 12:
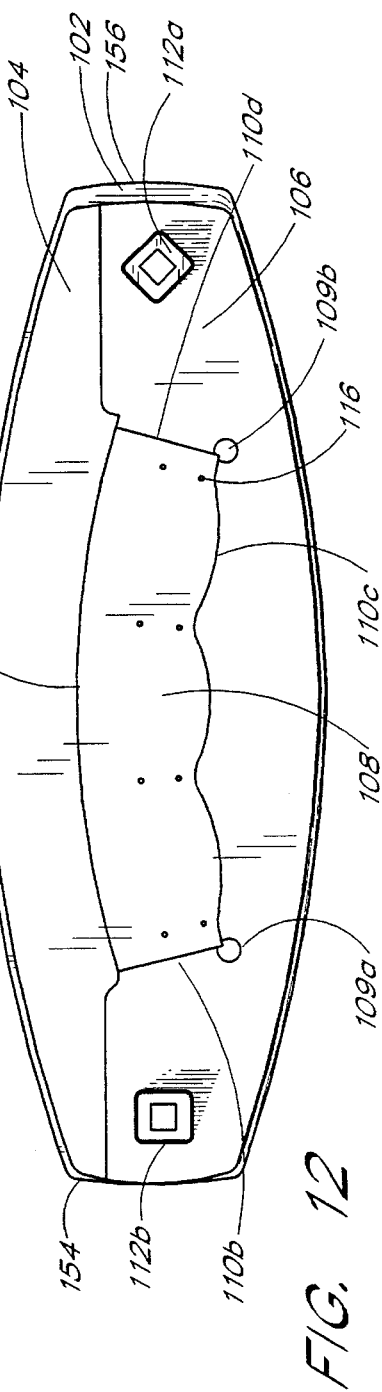
FIG. 12 is a bottom view of the cutting die assembly.

As shown in FIGS. 9 and 12, insert 108 is constructed to have a peripheral configuration corresponding to the desired configuration of the tissue after cutting. Blade retainers 104 and 106 have a corresponding interior geometry which permits insert 108 to be secured within blade retainers 104 and 106. In the preferred embodiment, blade retainers 104 and 106 completely surround the outer-side edges of insert 108, while leaving a gap between the edges of blade retainers 104 and 106 and the edges of insert 108. The gap is wide enough to accommodate and retain the cutting blades 110a–d, but narrow enough to prevent slippage of the blades 110a–d once the cutting die 100 is assembled and used. The blade retainers 104 and 106 and insert 108 define a substantially flat surface on the side nearest to the tissue when the cutting die assembly is inserted into the cutting base assembly.

In the preferred embodiment, blade retainers 104 and 106 are provided with structure which facilitates their joining to surround insert 108 and secure blade 110. As shown in FIG. 9, such structure may include a tongue 105 on each end of left-hand blade retainer 104, which is adapted to interlock with corresponding grooves 107 on each end of the right-hand blade retainer 106. Advantageously, tongues 105 and grooves 107 allow for precise alignment of the blade retainers 104 and 106 when they are locked together by inserting tapered dowels 112 into tapered throughholes 118 in the tongue 105 and grooves 107. However, as can be appreciated by one of skill in the art, other structures may be used to join blade retainers 104 and 106.

A significant feature of the invention, as shown in FIG. 12, is that the two corners of the blade retainer 106 are relieved by two through holes 109a and 109b. As shown in FIG. 12, the end of the blade 110c extends into through holes 109a and 109b with the adjoining blades 110b and 110d abutted up against. Without the relief holes 109a and 109b, the precise juncture of these blades would involve such tight tolerances that manufacturing practices typically would dictate a slight gap between the blades. Dies constructed with gaps between adjoining blades leave a small segment of uncut tissue at the corners of the opening, requiring a manual cut after opening of the die to separate the two pieces of tissue.

Similarly, in the preferred embodiment, the juncture of blades 110a with 110b and 110d is also designed to eliminate gaps between the blades. As illustrated in FIG. 12, this is achieved by configuring blade retainers 104 and 106 such that an extra space is provided so that blade 110a may extend beyond the point which it joins blades 110b and 110c.

The preferred embodiment of the heart valve disclosed and claimed in the '955 patent provides an inner stent having tissue alignment members and three integral leaflets. Consequently, the preferred embodiment of this invention includes four pairs of ferrules 116 embedded in the cutting surface of insert 108. The location of ferrules 116 corresponds to the location of the tissue alignment members of the heart valve inner stent. The presently preferred material for ferrules 116 is a hypodermic needle formed from corrosion resistant stainless steel.

Ferrules 116 protrude slightly above the surface of insert 108, extending approximately 55 mils above the surface created by blade retainers 104 and 106 and insert 108. In addition, the diameter of the ferrules 116 corresponds to the diameter of the tissue alignment members.

The cutting blades 110 are fixedly retained within the narrow gap between the island 108 and the blade retainers 104 and 106. The presently-preferred blade material is 301 stainless steel with a half-hard temper, measuring approximately 0.005 inches in thickness, and 0.312 inches in height. In the preferred embodiment, the cutting blades extend approximately 55 mils above the surface formed by blade retainers 104 and 106 and insert 108.

Figure 10:
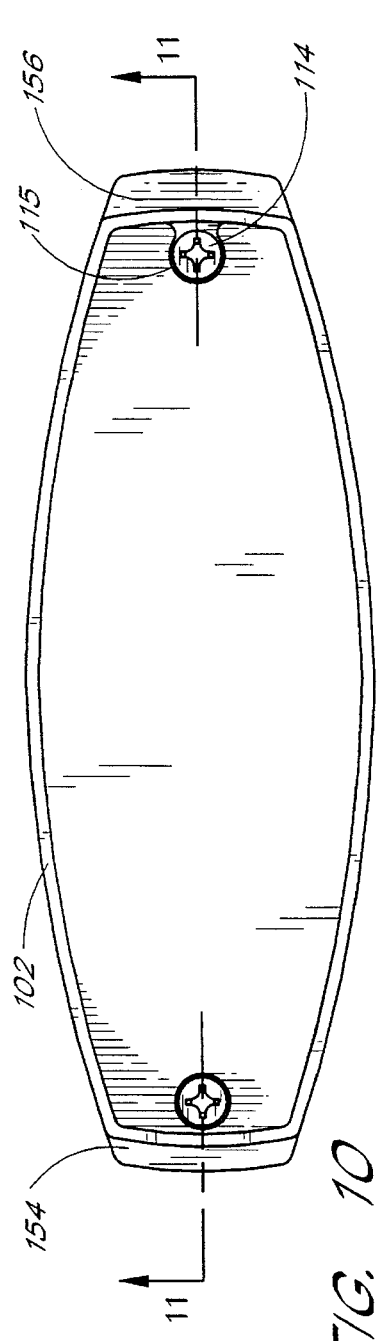
FIG. 10 is a top view of the cutting die assembly.
Figure 11:
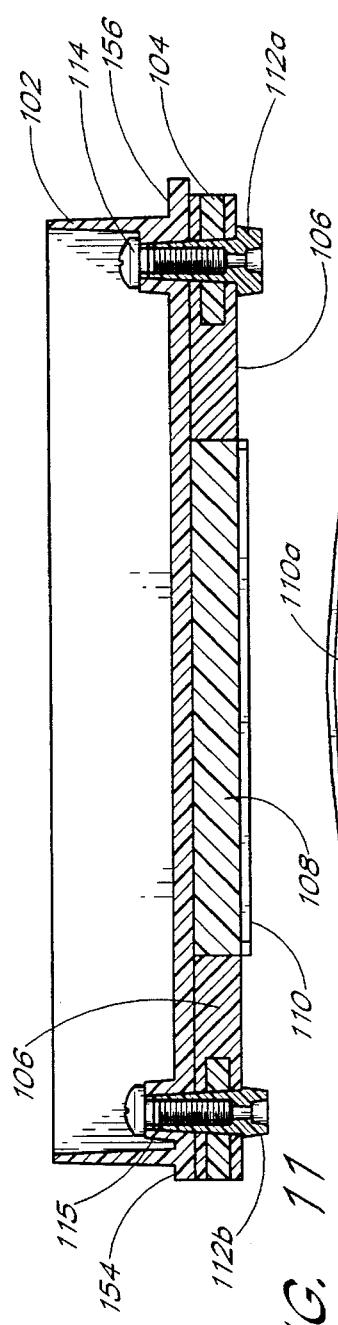
FIG. 11 is a cross-sectional view of the cutting die assembly of FIG. 10.

The handle 102 is provided with attachment holes 115 on either end, as shown in FIGS. 10 and 11, and is attached to the blade retainers 104 and 106 by attachment screws 114. Preferably, screws 114 are self-tapping and are threaded into tapered dowels 112, thereby pulling dowels 112 into tapered holes 118 to securely interlock the blade retainers 104 and 106. Optimally, handle 102 has a shape and size which allow it to be easily gripped by the operator during the cutting operation, such as modified rectangular shape depicted in FIG. 9.

As can be seen from FIGS. 9 and 12, tapered dowels 112 have a square head. The orientation of each of the heads 112a and 112b of tapered dowels 112 differs, head 112a being rotated approximately 45° with respect to head 112b. This orientation of the dowel heads 112a and 112b ensures the cutting die assembly 100 is correctly aligned when it is inserted into the cutting base assembly 120, as will be described below. Tapered dowels 112 may be formed of any suitable biocompatible material with sufficient lubricity to allow the dowels 112 to be seated in holes 118, such as DELRIN manufactured by DuPont Chemicals.

In a preferred embodiment, handle 102 includes a right flange 154 and a left flange 156, which protrude from the body of handle 102. The respective lengths of the right and left flanges 154 and 156 are unequal, with flange 156 extending outwardly farther than flange 154 as depicted in FIG. 10. The leading edges of flanges 154 and 156 are advantageously tapered slightly (not shown) to facilitate insertion of the cutting die assembly 100 into the cutting base assembly 120.

Figure 13:
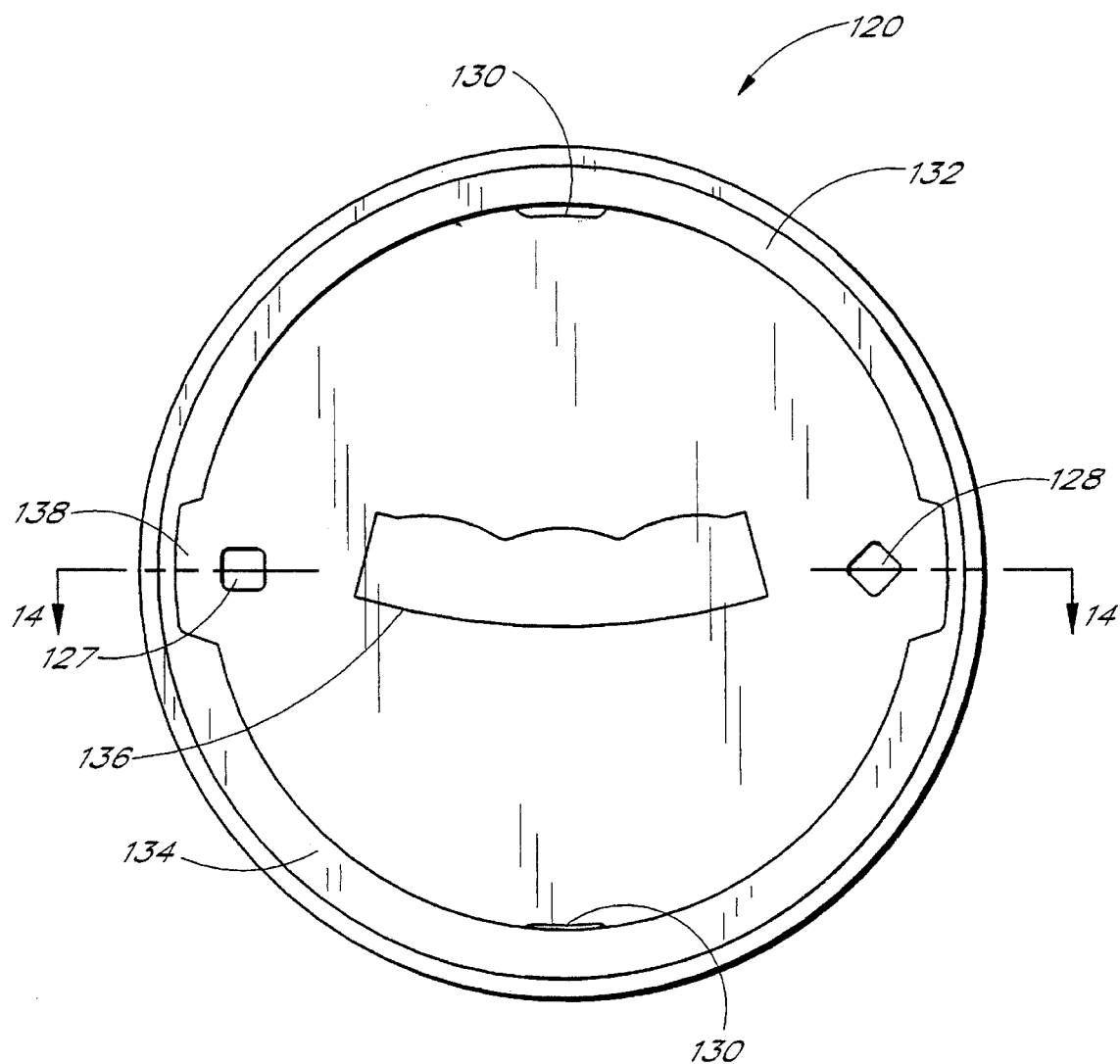
FIG. 13 is a top view of the cutting base assembly of FIG. 7.
Figure 14:
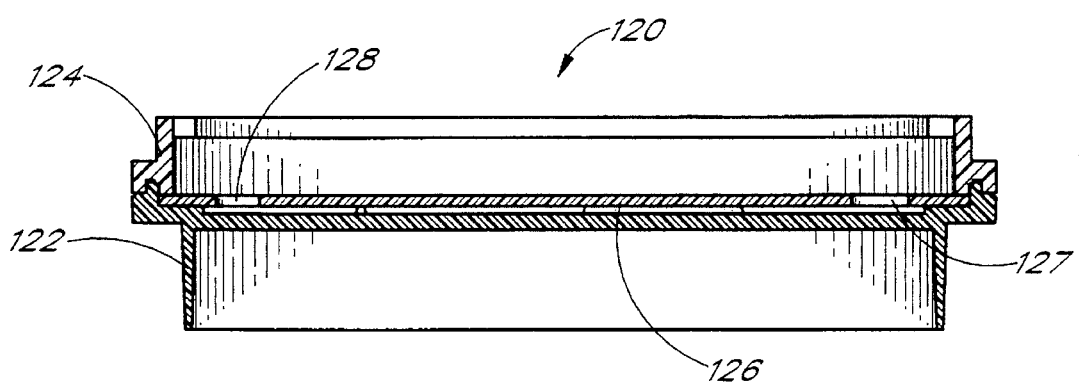
FIG. 14 is a cross-sectional view of the cutting base assembly of FIG. 13.

As seen in FIGS. 13 and 14, the cutting base assembly 120 includes a base 122, a die guide 124, and a cutting pad 126. In the preferred embodiment, base 122 and die guide 124 are made from a medical grade polycarbonate which has been filled with about 30% glass fibers to provide increased rigidity.

During the manufacture of the cutting base assembly 120, cutting pad 124 is placed on the upper surface of base 122, and then die guide 124 is attached to base 122, thereby securing cutting pad 126 within a groove 125 formed between the cutting base 122 and the die guide 124. Die guide 124 may be attached to base 122 by any method known to those of skill in the art. For example, die guide 124 may be ultrasonically welded to base 122. Cutting pad 126 is then free to rotate within groove 125, but is held in an initial alignment by a detent feature 130 which rests in a corresponding notch (not shown) in cutting die guide 124, until pad 126 is rotated by the user. The cutting pad 126 may be made from any medical grade material with sufficient lubricity to rotate within the groove 125 formed by the base 122 and die guide 124, and which also permits embedding of blades 110. In the preferred embodiment, pad 126 is formed of TEFLON.

Referring to FIG. 13, the cutting die guide 124 is an annular structure having upper lips 132 and 134. A pair of notches 138 are formed in upper lips 132 and 134 to allow insertion of the cutting die assembly 100 into the cutting base assembly 120. The leading edges of notches 138 are advantageously tapered (not shown) so that flanges 154 and 156 are directed under lips 132 and 134 when cutting die assembly 100 is first rotated. After rotation has begun, flanges 154 and 156 and lips 132 and 134 cooperate to prevent cutting die assembly 100 from being prematurely removed from cutting base assembly 120.

In a preferred embodiment, lip 134 has a greater width than does lip 132. Advantageously, this prevents rotation of the cutting die assembly 100 beyond 180°, and limits the direction of rotation to the clockwise direction, during operation of the device because the cutting die assembly 100 will not rotate past the point at which handle flange 156 encounters the shorter lip 132 on the cutting die guide 124.

Two square holes 127 and 128 are formed on cutting pad 126. As seen in FIG. 13, the holes 127 and 128 are rotated 45° with respect to each other and correspond in shape and size to the heads 112a and 112b on tapered dowels 112. Advantageously, the presence of holes 127 and 128 requires that dowel heads 112a and 112b be aligned to insert cutting die assembly 100 into the cutting base assembly 120, thereby restricting the cutting die assembly 100 to one of two possible insertion orientations with respect to the cutting base assembly 120.

The shape and location of the tissue area to be cut is indicated on the cutting pad by markings 136, which aid the operator in positioning the harvested tissue so that it can be properly cut.

Figure 15:
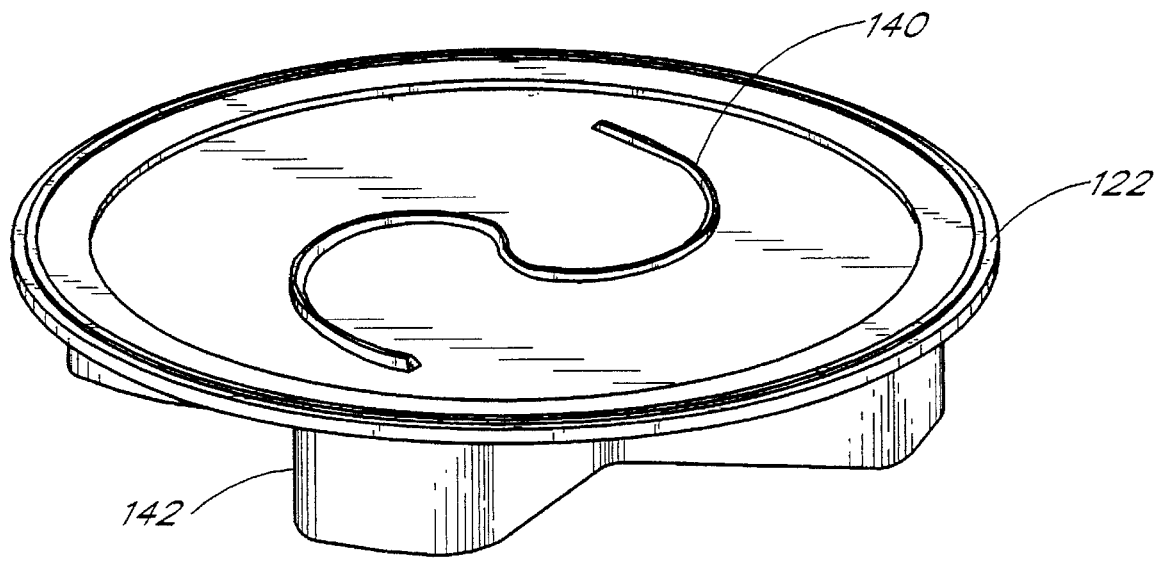
FIG. 15 is a perspective view of the cutting base illustrating the cutting bump on the upper surface of the cutting base.

Referring to FIG. 15, the upper surface of base 122 includes a cutting bump 140. As can be seen in FIGS. 14 and 15, cutting bump 140 is positioned directly below cutting pad 126 in the cutting base assembly 120. During the cutting operation, cutting bump 140 forces the cutting pad, on which the tissue is mounted, against blades 110. The shape of the cutting bump 140 is chosen so that the entire surface of the cutting blade 110 is swept by the cutting bump 140 after 180° rotation of the cutting die assembly 100. In the preferred embodiment, as illustrated in FIG. 15, the cutting bump has a spiral shape.

Figure 16:
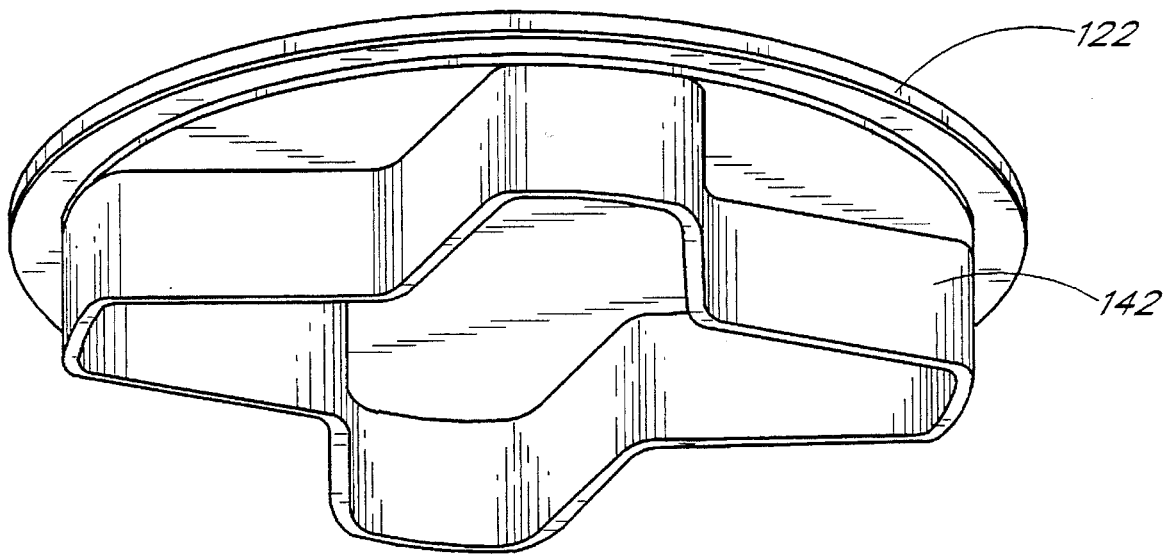
FIG. 16 is a bottom perspective view of the cutting base, illustrating the molded grip on the lower surface of the base.

The lower surface of cutting base 122 is provided with an integrally molded grip 142, as shown in FIG. 16. Grip 142 can assume a variety of shapes, provided that shape chosen allows the user to firmly grasp the cutting base during the cutting operation.

To operate the rotary tissue cutting die of the present invention, the user places a harvested patch of tissue on the cutting pad 126 and positions the tissue by aligning it with markings 136 on the cutting pad 126. The cutting die assembly 100 is then inserted into cutting base assembly 120 by aligning flanges 154 and 156 (see FIGS. 10 and 11) with notches 138, and dowel heads 112a and 112b (see FIGS. 11 and 12) with holes 127 and 128 (see FIGS. 7 and 13). The user then grips handle 102 with one hand, and molded grip 142 with the other hand, and rotates the cutting die assembly 100 as it is then attached cutting pad 126 carrying the tissue approximately 180° with respect to the cutting base 122.

The tissue placed on cutting pad 126 is cut by the action of the cutting bump 140 sweeping the blade profile as the cutting die assembly 100 is rotated relative to the cutting base 122. The cutting bump 140 forces the tissue and the cutting pad 126 into the blade 110, causing the tissue to be cut and the blade to be embedded in the cutting pad 126 a short distance, thus assuring a complete cut of the tissue. As described above, the cutting die assembly 100 is restricted from moving away from the cutting base assembly 120 by flanges 154 and 156 and lips 132 and 134 after rotation has begun.

Numerous variations and modifications can be made without departing from the spirit of the present invention. Therefore, it should be clearly understood that the forms of the present invention described above and shown in the figures of the accompanying drawings are illustrative only and are not intended to limit the scope of the present invention.

What is claimed is:

1. An apparatus for cutting tissue to be used in a heart valve, said heart valve having an inner stent configured with a plurality of posts, each of said posts including outwardly-projecting tissue alignment members, and an outer stent having a plurality of posts and an expandable base with tensioning means, said inner stent positioned inside said outer stent, said outer stent tensioning means providing a clamping force securing said inner stent, said apparatus comprising:

a cutting die assembly including a handle with a plurality of attachment points, a first blade retainer and a second blade retainer, said blade retainers adapted to be attached to said handle at said attachment points;

an insert positioned within said blade retainers such that a narrow gap exists between said insert and said blade retainers, said insert further having a peripheral configuration corresponding to the configuration into which the tissue will be cut;

a blade with a razor sharpened edge retained within said gap, said blade edge extending above the surface defined by said insert and said blade retainers;

a plurality of attachments provided to secure said handle to said blade retainers;

a base assembly adapted to receive said cutting die assembly, said base assembly including a cutting base having a substantially circular upper surface and a molded lower surface, said upper surface having a raised portion comprising a cutting bump;

a circular cutting pad with an upper face and a lower face, said pad positioned on said upper surface of said cutting base and adapted to be rotated thereon, said cutting bump being adapted to contact said lower face when said pad is rotated, wherein said contact forces said blade edges into contact with the upper face of said cutting pad so that tissue retained between said blade edges and said upper face is cut; and an annular cutting die guide fixedly secured to the upper surface of said cutting base, such that said cutting pad is rotatably retained between said cutting base and said cutting die guide.

2. The apparatus of claim 1, wherein said insert further comprises a plurality of raised ferrules positioned to cut holes into the tissue in locations corresponding to said tissue alignment members on said inner stent.

3. The apparatus of claim 2, wherein said ferrules extend 55 mils above the surface of said blade retainers and said insert.

4. The apparatus of claim 1, wherein said blade retainers further comprise a plurality of through holes, said through holes formed at one or more of the corner junctions of said blade retainers and said insert.

5. The apparatus of claim 1 wherein said handle, said blade retainers, and said insert are made of medical-grade translucent polycarbonate.

6. The apparatus of claim 1 wherein said blade is made of a high quality corrosion resistant metal.

7. The apparatus of claim 6 wherein said blade is about 0.005 inch thick and made of stainless steel.

8. The apparatus of claim 1 wherein said blade extends 55 mils above the surface of said blade retainers and said insert.

9. The apparatus of claim 1, wherein said handle includes a first flange on one end, and a second flange on the opposite end, and where the length of said first flange is greater than that of said second flange.

10. The apparatus of claim 1, wherein said annular cutting die guide includes a first and second lip divided by a pair of notches positioned on opposite sides of said die guide, where the width of said first lip is greater than the width of said second lip.

11. The apparatus of claim 1, wherein said cutting bump has a spiral shape and sweeps the profile of said blade edges as the cutting die assembly is rotated 180 degrees with respect to said cutting base.

12. The apparatus of claim 1, wherein the juncture of said cutting base and said cutting die guide forms a groove within which said cutting pad may rotate.

13. The apparatus of claim 1, wherein said cutting pad includes a detent which prevents said cutting pad from rotating in the absence of an applied rotational force by the user.

14. The apparatus of claim 1, wherein said blade is comprised of four separate blades.

15. An apparatus for quickly and precisely cutting a piece of tissue to a predetermined configuration, said apparatus comprising:

a cutting die assembly including a handle, a first blade retainer and a second blade retainer, wherein said blade retainers are attached to said handle;

an insert positioned within said blade retainers, wherein a narrow gap remains between the outer edges of said insert and said blade retainers, and said insert and blade retainers define a substantially flat surface on the side of said insert and said blade retainers which contacts said tissue;

a blade defining the perimeter of the desired tissue configuration, said blade retained by said blade retainers within said narrow gap, said blade having edges which extend beyond said surface;

a cutting base assembly having a rotatable cutting pad for placing said tissue to be cut, said base adapted to receive said cutting die assembly such that said blade edges may contact tissue placed on said pad;

wherein said tissue is cut when a cutting bump on said cutting base sweeps said pad over the profile of said blade edge thereby causing said blade edge to pass through said tissue and to embed in said pad.

16. An apparatus for quickly and precisely cutting a piece of tissue to a desired spatial configuration, said apparatus applying a consistent cutting force substantially independent of the force applied by the operator so that the tissue is substantially completely cut through along the perimeter of said desired spatial configuration, said apparatus comprising:

a cutting die;

a blade defining the perimeter of the desired spatial configuration, said blade supported by said cutting die;

a cutting base member adapted to receive said cutting die, said cutting base member including a lower surface and an upper surface having a cutting bump formed thereon;

a cutting pad rotatably mounted on said cutting base member, said cutting pad adapted to be deflected upward by said cutting bump into said blade when said cutting die is inserted into said cutting base member and said cutting pad is rotated.

17. A method for precisely cutting a piece of tissue into a predetermined shape comprising the steps of:

providing a roughly sized piece of tissue;

providing a tissue cutting die having raised blades for cutting said piece of tissue and a cutting base member with a cutting bump covered by a rotatable cutting pad, where said cutting pad has an upper face and a lower face;

laying said roughly sized piece of tissue flat across said upper face of said cutting pad;

inserting said cutting die guide into said cutting base member, such that said blade is disposed above said tissue;

rotating said cutting die guide within said base member to cause said cutting bump to deflect said lower face upward, thereby forcing said pad into said blade and cutting said tissue;

disassembling said cutting die and said base member and removing said tissue therefrom.

18. The method of claim 17, wherein said blades cut said tissue by shearing.

19. The method of claim 18, wherein said shearing is caused by said a spiral shaped cutting bump sweeping the blade profile and deflecting said cutting pad into said blade as said cutting die is rotated relative to said cutting base member.

* * * * *